(12) United States Patent
Janata et al.

(10) Patent No.: US 8,562,806 B2
(45) Date of Patent: Oct. 22, 2013

(54) ELECTROCHEMICAL BIOSENSOR ARRAYS AND INSTRUMENTS AND METHODS OF MAKING AND USING SAME

(75) Inventors: Jiri Janata, Atlanta, GA (US); Miroslava Josowicz, Atlanta, GA (US); George Yang Yu, Chattanooga, TN (US)

(73) Assignee: Georgia Tech Research Corporation, Atlanta, GA (US)

( * ) Notice: Subject to any disclaimer, the term of this patent is extended or adjusted under 35 U.S.C. 154(b) by 430 days.

(21) Appl. No.: 12/671,515

(22) PCT Filed: Jul. 31, 2008

(86) PCT No.: PCT/US2008/071849
§ 371 (c)(1),
(2), (4) Date: Jan. 31, 2010

(87) PCT Pub. No.: WO2009/018496
PCT Pub. Date: Feb. 5, 2009

(65) Prior Publication Data
US 2010/0197524 A1      Aug. 5, 2010

Related U.S. Application Data

(60) Provisional application No. 60/953,119, filed on Jul. 31, 2007.

(51) Int. Cl.
G01N 33/543    (2006.01)
G01N 27/26     (2006.01)
C12M 1/40      (2006.01)
C40B 60/00     (2006.01)

(52) U.S. Cl.
USPC .............. 204/600; 435/287.1; 435/287.2; 422/68.1; 422/82.01

(58) Field of Classification Search
USPC .............. 204/450, 600; 435/6, 287.1, 287.2; 257/253; 422/68.1, 82.01
See application file for complete search history.

(56) References Cited

U.S. PATENT DOCUMENTS

2002/0085954 A1 * 7/2002 Havens et al. ............ 422/63
2002/0195345 A1 * 12/2002 Bentsen et al. ........... 204/600

FOREIGN PATENT DOCUMENTS

| WO | WO 2004/021010 | * | 3/2004 |
| WO | WO 2005/040404 | * | 5/2005 |
| WO | WO 2006/032158 | * | 3/2006 |

OTHER PUBLICATIONS

Thompson et al. (J.AmChem.Soc. 2003, 125, 324-325).*
Kricka (Clinical Chemistry 44:9, 2008-2014 (1998)).*
Hartung et al. (Journal of The Electrochemical Society, 152, 2005, pp. 345-350).*
Aiyejorun et al. (Journal of Chemical Education, vol. 83, No. 8, Aug. 2006, 1208-1211).*

* cited by examiner

Primary Examiner — J. Christopher Ball
Assistant Examiner — Jennifer Dieterle
(74) Attorney, Agent, or Firm — Troy S. Kleckley; Ryan A. Schneider, Esq.; Troutman Sanders LLP

(57) ABSTRACT

Improved electrochemical biosensor arrays and instruments are disclosed herein. Methods of making and using the electrochemical biosensor instruments are also disclosed. An electrochemical biosensor array can include an array of microelectrodes disposed on a substrate. Each microelectrode can include a conducting electrode material disposed on a portion of the substrate, a first polymeric layer disposed on at least a portion of the conducting electrode material, a second polymeric layer disposed on at least a portion of the first polymeric layer, and a capture molecule that is in physical communication with the second polymeric layer.

11 Claims, 11 Drawing Sheets

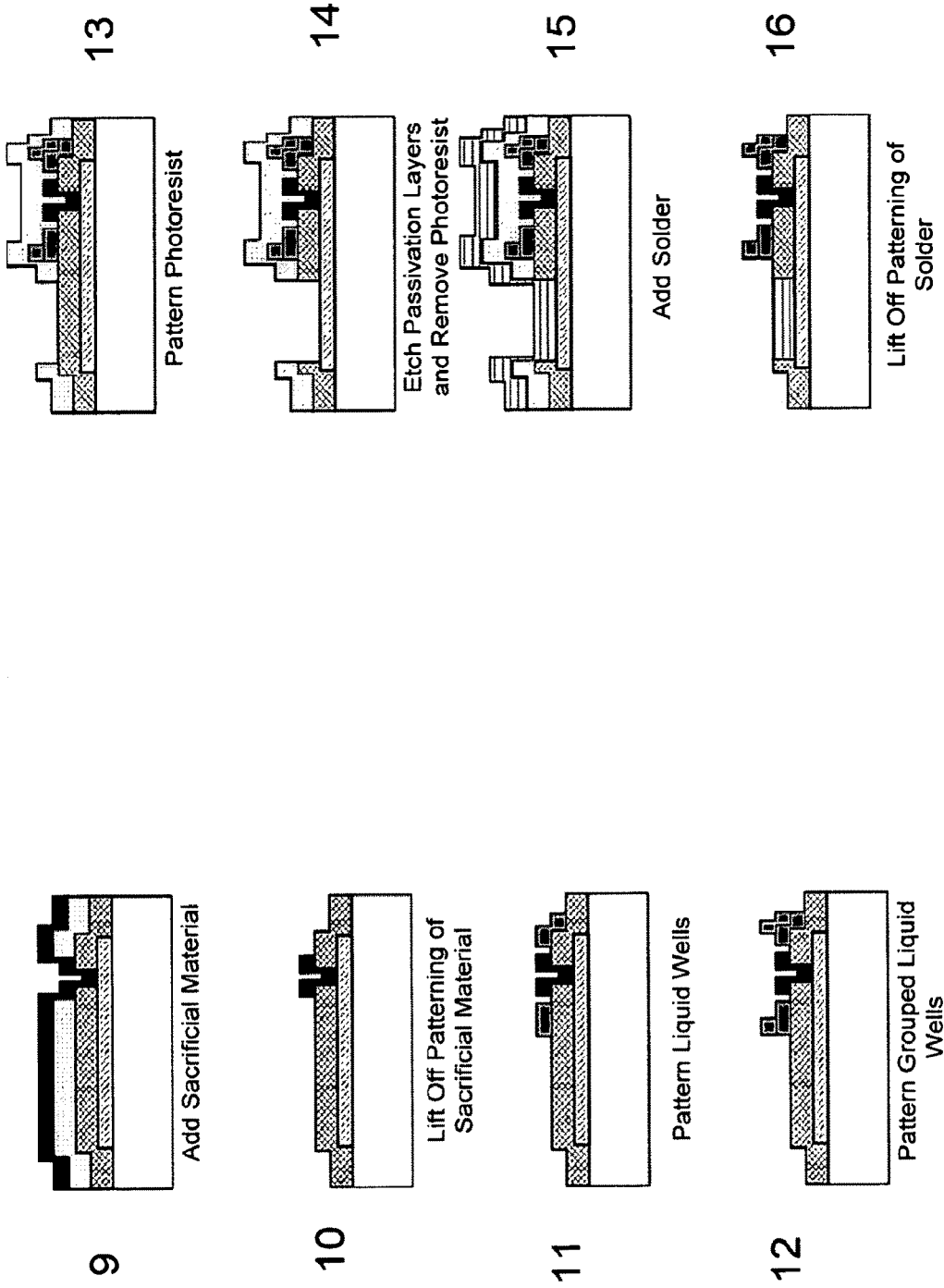

ELECTROCHEMICAL BIOSENSOR ARRAYS AND INSTRUMENTS AND METHODS OF MAKING AND USING SAME

CROSS-REFERENCE TO RELATED APPLICATION

The present application is a United States National Stage Application of International Patent Application Ser. No. PCT/US2008/071849, filed 31 Jul. 2008, and entitled "Electrochemical Biosensor Arrays and Instruments and Methods of Making and Using Same," which claims the benefit of U.S. Provisional Patent Application Ser. No. 60/953,119, filed 31 Jul. 2007, and entitled "Electrochemical Biosensor Instruments and Methods of Making and Using Same," the entirety of both of which are hereby incorporated by reference as if fully set forth below.

TECHNICAL FIELD

The various embodiments of the present invention relate generally to biosensors, and more particularly, to electrochemical biosensor arrays and instruments, and to methods of making and using the instruments.

BACKGROUND

In general, a biosensor is a device capable of identifying a target biomolecule such as a polynucleotide, polypeptide, or other biomolecule of interest. There is great interest in developing biosensors to be used for varied purposes from disease diagnostics to monitoring gene expression in organisms to identification and speciation of possible pathogens and/or biocontaminants to the identification of drug candidates. Such devices would be a great benefit for medical diagnostics, food and water safety monitoring, and defense of military and civilian populations from biological threats. Sensors developed for the detection of biological analytes are typically based on ligand specific binding events between a recognition binding pair, such as antigen-antibody, hormone-receptor, drug-receptor, cell surface antigen-lectin, biotin-avidin, and complementary nucleic acid strands. The analyte to be detected may be either member of the binding pair, or the target analyte may be a ligand analog that competes with the ligand for binding to the complement receptor.

Traditional biosensors designed for the purpose of detecting binding events between complementary binding pairs, such as those described above, are large, and require significant volumes of liquid reagents and highly trained personnel. Typically, the reduction or elimination of any of these requirements leads to a subsequent loss of sensitivity and/or selectivity. Over the past several years researchers have been striving to develop alternatives to current biosensor technologies, but many developments have been geared to large, array-based equipment to increase sensitivity or throughput in the laboratory setting.

Examples of some of these efforts include optical biosensors that employ recognition elements to detect a target analyte, such as nucleic acid (e.g., DNA or RNA) hybridization assays. Such hybridization assays have been developed to interrogate samples for multiple analytes from a single sample. Nucleic acid based biosensors can be very selective; however, the optical techniques employed in many such sensors require multiple liquid reagents that must be stored in controlled environments and fluorescent labels that can be unstable. Labeling of biological molecules can be very expensive and produce low yields. Also the need for optics to excite or collect fluorescent signal adds expensive and complicated components and creates alignment issues. It would be desirable to reduce the reagent load, remove the fluorescent labels, reduce manufacturing and operational costs and make the sensing element reusable and/or portable.

Biosensors incorporating electrochemical techniques were developed in order to meet some of these needs. A typical electrochemical biosensor includes a base electrode and a biochemically discriminating element in contact or otherwise coupled to the electrode. The biochemically discriminating element functions either to detect and transform the target analyte into an electrically active species, which is then detected by the electrode, or to otherwise generate an electrical signal, which is sensed and monitored by the electrode.

The application of electrochemical techniques to biosensor technology holds many advantages over optical techniques including, but not limited to, the lack of optical elements to align, the ability to operate in turbid media such as blood or waste water, as well as the ability to capitalize on the vast electronics processing industry for electrode arrays and control electronics. However, manufacture and use of such electrochemical biosensors has proven challenging due to complicated designs and electrochemical interferences caused by interactions of substances other than the target analyte.

Owing to the difficulty of converting a biochemical binding event into an electrochemical signal, early applications of electrochemical biosensors were designed for detecting analytes that are themselves electrochemical species, or that can participate in reactions that generate electrochemical species, rather than to direct detection of ligand-receptor binding events. However, such sensors are quite limited in their application. In an effort to overcome this problem, sensors were developed that involve an intermediate reaction or a secondary active species of some sort, which acts to generate the electrochemical signal. One such design includes two separate reaction elements in the biosensor: a first element contains a receptor and bound enzyme-linked ligand, and the second element includes components for enzymatically generating and then measuring an electrochemical species. In operation, analyte ligand displaces the ligand-enzyme conjugate from the first element, releasing the enzyme into the second element region, thus generating an electrochemical species that is measured in the second element. Two-element biosensors of this type are relatively complicated to produce, thus limiting their usefulness.

Biosensors that attempt to couple electrochemical activity directly to a ligand-receptor binding event without the use of two reaction elements have been proposed where a lipid bi-layer membrane containing an ion-channel receptor that is either opened or closed by ligand binding to the receptor controls access to the electrode. Electrodes of this type have been limited at present to a rather small group of receptor proteins.

Additionally, there is a need for biosensors, particularly for diagnostic purposes, which are easily portable for use in the field rather than the laboratory setting. Such a biosensor would provide many advantages for use in areas and situations where laboratory access is limited, such as in third world countries, or in situations where time does not permit sending a sample to a lab for analysis and waiting for results.

As discussed, many of the above techniques have disadvantages such as complicated designs, expensive reagents and manufacturing costs, use of fluorescent tags, applicability to only a small class of biomolecules, and complicated multistep processing. Thus, there is a need for a biosensor that overcomes at least these disadvantages.

BRIEF SUMMARY

Various embodiments of the present invention are directed to improved electrochemical biosensor arrays and instruments. Some embodiments are also directed to methods of making the improved electrochemical biosensor arrays and instruments. Still some other embodiments are directed to methods of using the improved electrochemical biosensor arrays and instruments.

An electrochemical biosensor array, according to some embodiments, can include an array of microelectrodes disposed on a substrate. Each microelectrode in the array can include a conducting electrode material disposed on a portion of the substrate. A first polymeric layer can be disposed on at least a portion of the conducting electrode material. Similarly, a second polymeric layer can be disposed on at least a portion of the first polymeric layer. Each microelectrode can also include a capture molecule in physical communication with the second polymeric layer. The substrate can be sufficiently insulating as to prevent electrical communication between any two microelectrodes of the array.

A biosensor instrument, according to some embodiments of the present invention, can include a biosensor array and a printed circuit board. The biosensor array includes an array of microelectrodes disposed on a substrate. The substrate can be sufficiently insulating as to prevent electrical communication between any two microelectrodes of the array. Each microelectrode can include a conducting electrode material disposed on a portion of the substrate and a connection point material disposed on a different portion of the substrate. A first polymeric layer can be disposed on at least a portion of the conducting electrode material, a second polymeric layer can be disposed on at least a portion of the first polymeric layer, and a capture molecule can be in physical communication with the second polymeric layer. The printed circuit board can include signal processing circuitry and a plurality of connection points. The number of connection points on the printed circuit board corresponds to the number of connection points of the biosensor array. The connection points of the biosensor array can be bound to the connection points of the printed circuit board. A reaction vessel for the microelectrodes of the biosensor array can be formed by the bond between the biosensor array and the printed circuit board.

A method of making a biosensor array, according to some embodiments of the present invention can include depositing a plurality of conducting electrode materials on separate portions of a substrate. The substrate can be sufficiently insulating as to prevent electrical communication between any two microelectrodes of the array. The method can also include depositing a first polymeric layer on at least a portion of each of the conducting electrode materials. A second polymeric layer can be deposited on at least a portion of each of the first polymeric layers. A capture molecule that is capable of being bound to at least a portion of a second polymeric layer can be provided.

A method of making another biosensor array, according to some embodiments of the present invention, can include providing a substrate that has an array of at least two repeating units on the substrate. Each repeating unit can include a working microelectrode that has an electrode support. A first polymer layer can be polymerize adjacent to the working microelectrode, and a second polymer layer can be polymerized adjacent to the first polymer layer. The biosensor array can be exposed to a solution of a capture molecule so as to allow the capture molecule to attach to the second polymer layer. The second polymer layer can include a pendant phosphonate group and the method can also include functionalizing the second polymer layer with a multivalent metal cation, such that the capture biomolecule attaches to the multivalent metal cation to form a surface-immobilized complex.

A method of fabricating a biosensor instrument, according to some embodiments of the present invention, can include depositing a plurality of conducting electrode materials on separate portions of an insulating substrate that is sufficiently insulating to prevent electrical communication between two microelectrodes of the array. A first polymeric layer can be deposited on at least a portion of each of the plurality of conducting electrode materials. A second polymeric layer can be deposited on at least a portion of each of the first polymeric layers. The method can also include providing a capture molecule capable of being bound to at least a portion of a second polymeric layer. The substrate can also be connected to a printed circuit board in such a matter as to define a reaction vessel by the connection.

During operation, the biosensor instrument can be contacted with a solution including an electrolyte of a buffer solution containing ions. A flow of electrons can be provided to the biosensor instrument, and a voltammetric current can be monitored and reported by a signal processing mechanism that is coupled to the biosensor instrument. The biosensor can be contacted with a second solution including an electrolyte of buffer solution containing ions and a target analyte, and the voltammetric current can be monitored and reported by the signal processing mechanism that is coupled to the biosensor instrument. Any change in the voltammetric current can be monitored and reported by the signal processing mechanism. A specific change in the voltammetric current can indicate a binding event and the presence of the target analyte.

Other aspects and features of embodiments of the present invention will become apparent to those of ordinary skill in the art, upon reviewing the following detailed description in conjunction with the accompanying figures.

BRIEF DESCRIPTION OF THE DRAWINGS

Aspects of the disclosure can be better understood with reference to the attached drawings, described in greater detail below. The components in the drawings are not necessarily to scale, emphasis instead being placed upon clearly illustrating the principles of the present disclosure.

DETAILED DESCRIPTION

Figure 1:
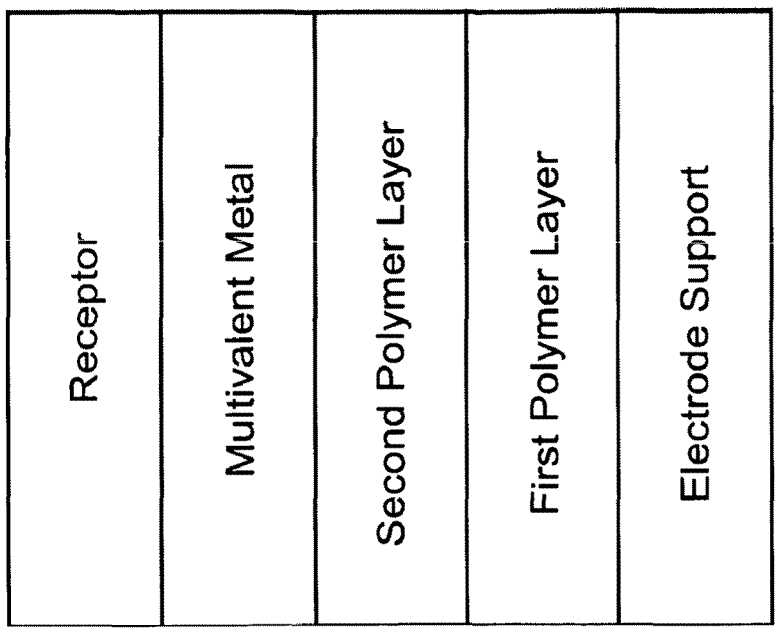
FIG. 1 schematically illustrates a microelectrode of a biosensor array according to some embodiments of the present invention.

Referring now to the figures, wherein like reference numerals represent like parts throughout the several views, exemplary embodiments of the present invention will be described in detail. Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented.

As used herein, the terms "first," "second," and the like, "primary," "secondary," and the like, do not denote any order, quantity, or importance, but rather are used to distinguish one element from another. Further, the terms "a", "an", and "the" do not denote a limitation of quantity, but rather denote the presence of "at least one" of the referenced item.

The various embodiments of the present invention provide improved electrochemical biosensor arrays and biosensor instruments. Methods of making and using the electrochemical biosensor arrays and instruments are also provided. Embodiments of the present disclosure are capable of providing inexpensive, simple, compact, or portable biosensor arrays and/or instruments, methods of making such devices, and methods of using the devices to detect a target analyte. There is a great need for this type of technology for applications including, but not limited to, medical diagnostics, military and civilian security, environmental safety, genetic mapping, and drug discovery, and a particular need for such applications in the field (or other non-laboratory) setting. The biosensor arrays and instruments of the present disclosure can provide a number of advantages including, but not limited to, low cost of manufacture, relatively easy assembly out of inexpensive and stable reagents, low operating costs owing to a low-power platform, the ability to manufacture the devices in small sizes, the ability to incorporate the devices and diagnostic analysis capabilities in a portable system, or the adaptability to producing a plurality of sensors in an array format on a single platform or chip for high-throughput applications.

As will be described in more detail below, the biosensor devices can be used to detect any chemical or biochemical target analyte. A biosensor array generally includes a substrate having an array of at least two repeating units on the substrate. Each repeating unit can include a working microelectrode, such as the one schematically shown in FIG. 1, having an electrode material, a first polymer layer adjacent to the electrode material, a second polymer layer adjacent to the first polymer layer, and one or more receptors or capture molecules coupled to the surface of the second polymer layer. The capture molecules can be coupled to the second polymer layer via a multivalent metal cation.

The capture molecules can be specific for one or more target analytes such that the biosensor can be capable of detecting an interaction event between the capture molecule and a target analyte.

Figure 2:
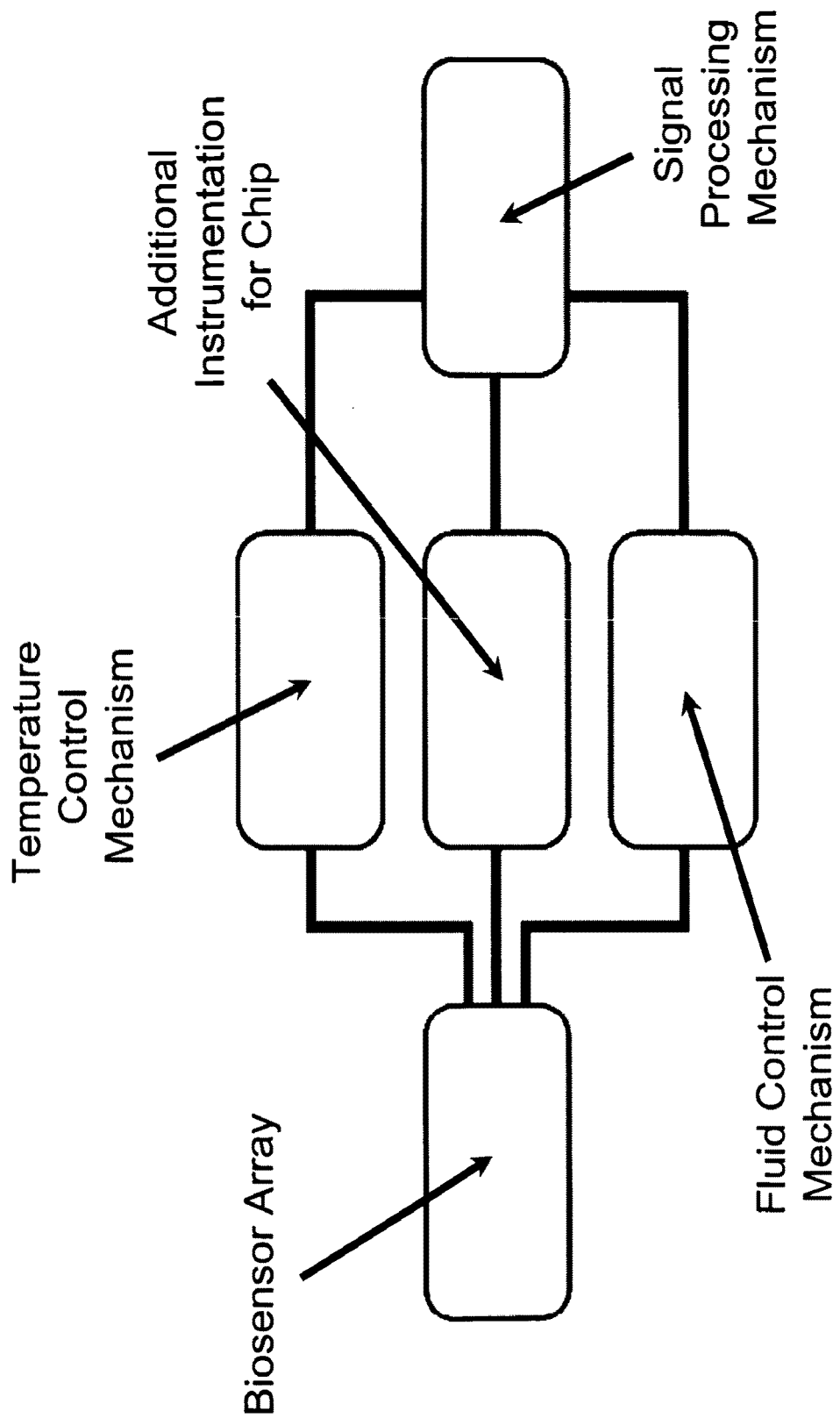
FIG. 2 schematically illustrates a biosensor instrument according to some embodiments of the present invention.

A biosensor instrument, such as the one shown schematically in FIG. 2, generally includes the biosensor array and also includes one or more of a temperature control mechanism, a fluid control mechanism, additional instrumentation for the biosensor array (e.g., signal processing circuitry, a reference electrode, a counter electrode, a potentiostat, and/or an electrochemical workstation), and a signal processing mechanism (e.g., a personal computer, mainframe, portable computer, personal data assistant, or the like), each of which could be in operative communication with one or more of the other components.

By way of example, the biosensor instrument can be configured such that the biosensor array is coupled to an electrochemical workstation that provides a current or voltage source to the electrodes to effect a flow of electrons to the biosensor array that is monitored and measured at the workstation by a computer, which reports and records the voltammetric current. The voltammetric current, and changes therein, can be recorded as a cyclic voltammogram. The computer system can include data transfer and evaluation protocol capable of transforming raw data from the biosensor array into information regarding the presence and/or absence of a target analyte. The computer can also be capable of providing diagnostic information regarding the target analyte. In certain situations, the computer is a portable personal computer that includes data transfer and evaluation software capable of storing and analyzing the recorded signals. Under these circumstances, the biosensor instrument can provide a diagnostic tool that itself is portable and is powered from the laptop computer.

The biosensor instruments of the present invention are capable of providing a specific electrochemical excitation signal that is optimized to yield the maximum diagnostic value. These biosensor instruments thus can represent a complete diagnostic package with the capability to aid rapid analysis by a person who has minimum technical training In exemplary embodiments, the raw electrochemical output from the biosensor array of the present disclosure is collected and transferred to the memory of a computer, which includes a pattern recognition evaluation program that can be "trained" to identify a specific binding event and also the degree of the matching between the capture molecule and the target analyte, and thus recognize the signature of a particular binding event for which it was "trained". Such a biosensor instrument provides a complete diagnostic package whose purpose is to aid rapid screening, detection, and analysis of a target analyte, without elaborate preparation, by a person who has minimum technical training and to enable portability of such a system, bringing heretofore unavailable diagnostic capabilities to remote areas.

Referring again to the working microelectrode of FIG. 1, the biosensor array comprises a substrate onto which the array of microelectrodes is disposed. The substrate can be formed of any material, provided that the material is not electrically conductive. More specifically, the substrate must be capable of providing insulation between each electrode of the array, so that there is no cross-talk between electrodes. Suitable substrate materials include, without limitation, ceramic materials, such as oxides (e.g., silica, fused silica, amorphous silica, fused amorphous silica, sapphire, or the like), nitrides (e.g., silicon nitride, boron nitride, or the like), carbides, oxycarbides, oxynitrides, or the like; polymeric materials (e.g., epoxies, phenolic papers, polyesters, or the like); fiberglass; or the like.

Each microelectrode generally includes an electrode material, a polymer bilayer, and a receptor molecule coupled to the surface of the second polymer layer of the polymer bilayer. In certain embodiments, the receptor and second polymer layer are coupled using a multivalent metal cation. For example, the multivalent metal cation can serve to bind the receptor and second polymer layer via a metal-ligand complex.

The electrode material (which can alternatively be termed herein an electrode support) is disposed on the substrate, either directly or by means of an adhesion layer interposed therebetween. The electrode support can be formed from any known electrode composition. Exemplary electrode materials include carbon, gold, platinum, silver, ruthenium, palladium, rhodium, osmium, iridium, or the like. In exemplary embodiments, the electrode material is platinum.

Where a large number of microelectrodes are included in the biosensor array, the thickness of the electrode support can vary from about 150 nanometers to about 5 micrometers. Otherwise, there are no constraints on the thickness of the electrode material. Depending on the size of the substrate and the number of microelectrodes in the array, the width of the electrode material for each microelectrode is generally less than or equal to about 200 micrometers.

Once the electrode material has been disposed on the substrate, the polymeric bilayer can be placed thereon. The components of the polymeric bilayer are generally polymerized (e.g., by electropolymerization, grafting, or the like) directly on the electrode material. It is desirable that the polymeric bilayer be chemically inert, and have good adhesion to the electrode material.

The ion transfer capability into and out of the polymeric bilayer is based on the electrochemically controlled exchange of the ions between the polymeric bilayer and the solution in which the target analyte is contained. The polymeric bilayer's ability to transfer anions is governed by the structure of its interface and by the applied potential. Simultaneously, the exchange of co-ions of the opposite polarity is hindered. Hence, the bilayer acts as electrochemically controlled ion exchanger.

The first polymer layer of the polymeric bilayer (i.e., the layer disposed on the electrode material) is the thicker of the two polymer layers. When this layer is polarized, it exchanges ions with the target analyte solution in a process called electrochemical doping. The ions exchanged are typically anions that are absorbed into the polymer when a positive potential is applied to the electrode and are expelled when a negative potential is applied. When the application of the potential is done in a cyclic manner, a cyclic voltammogram of a characteristic shape and size is obtained. It is possible to use other excitation waveforms, such as a "square wave cyclic voltammogram" that can enhance the interpretative potential of the electrochemical reaction.

A variety of electroactive polymers can be used for the first polymer layer, and one of skill in the art would understand the various polymers that could be used for this layer. By way of example only, some of the many suitable electroactive polymers include poly(aniline), substituted poly(aniline)s, polycarbazoles, substituted polycarbazoles, polyindoles, poly(pyrrole)s, substituted poly(pyrrole)s, poly(thiophene)s, substituted poly(thiophene)s, poly(acetylene)s, poly(ethylene dioxythiophene)s, poly(ethylenedioxypyrrole)s, poly(p-phenylene vinylene)s, or the like. Blends or copolymers or composites of an electroactive polymer can also be used. In exemplary embodiments, the first polymer layer is formed from polypyrrole.

Once the first polymer layer has been formed, the second polymer layer can be disposed directly on the first polymer layer. The purpose of the second polymer layer is to provide an improved mechanism for communication between the capture molecule and the electrode material. This layer will be thinner than the first polymer layer. For example, where the thickness of the first polymer layer is generally less than or equal to about 2 micrometers, the thickness of this polymer layer is generally less than 50 nanometers. In exemplary embodiments, the thickness of the first polymer layer is about 100 nanometers to about 1 micrometer, and the thickness of the second polymer layer is about 1 nanometer to about 10 nanometers.

The polymer of the second polymer layer is a so-called "self-doped" polymer.

Any self-doped polymer can be used for the second polymer layer, such polymers being known and understood by those skilled in the art to which this disclosure pertains. By way of example only, polymers that may form the backbone of these self-doped polymers include those that can be used in the first polymer layer, such as the polymers described above. A common feature of such compositions is the presence of a covalently bound acidic group that "self-dopes" the polymer. The covalently bound acidic group must have a very low solubility, or be insoluble, in any solution to which the biosensor array is exposed either during manufacture or during operation. An exemplary polymer, useful for this purpose includes, but is not limited to, poly 2,5,-bis (2-thienyl)-N-(3-phosphorylpropyl)pyrrole (pTPT), which has pendant phosphonate groups that can be separated from the main polymer backbone by about 3 to about 16 carbon atoms. Another exemplary polymer of this type is poly-1-(N-pyrrolyl)-10-decanephosphonic acid. Similar molecules with pendant phosphonate groups separated from the main polymer backbone by about 3 to about 16 carbon atoms can be used. Alternatively, the phosphonate group can be replaced by other anions that have a high affinity for multivalent cations. In exemplary embodiments, the second polymer layer is formed from pTPT.

In certain situations, the covalently bound acidic group that "self-dopes" the polymer of the second polymer layer can be used to form a salt when complexed with a multivalent metal cation. When implemented, the salt complex desirably is formed simultaneously at the surface of the polymer bilayer of each microelectrode in the array. Implementation of the multivalent metal cation can facilitate attachment of the capture molecule to the second polymer layer by ultimately forming a ligand-metal-ligand complex where the second ligand is the capture molecule (and any pendant groups that might be coupled thereto).

Any metal that exhibits more than one oxidation state can be used to form the complex between the capture molecule and the second polymer layer. The only limitation on the choice of metal is that when the multivalent metal cation is complexed with the acidic group of the polymer used for the second polymer layer, the corresponding salt must have a low solubility, or be insoluble, in any solution to which the salt is exposed either during manufacture or during operation. Otherwise, the metal will dissociate from the covalently bound acidic group. In exemplary embodiments, the multivalent metal cation is a magnesium or rare earth ion.

In order to complete the microelectrode, a capture molecule (alternatively termed herein a receptor, receptor molecule, probe, or capture probe) is placed on the surface of the bilayer. The capture molecule is generally one component of a recognition interaction complex, where the interaction may be direct or indirect and stems from an affinity of at least a portion of the target for at least a portion of the receptor. Another component of the recognition interaction complex is the target analyte (alternatively termed herein a target or target molecule) to be detected. In some instances, the detected composition can be an analog that competes with the intended target analyte for interaction with the receptor.

As used herein, the term "affinity" includes biological interactions and chemical interactions. The biological interactions can include, but are not limited to, bonding, adsorbing, or hybridizing. For example, when proteins are involved, a biological interaction can occur among one or more functional domains or regions (e.g., coiled coils, alpha-helices, beta-sheets, beta-barrels or the like) located on the target and/or the receptor. In this regard, the receptor or target can include one or more biological functional domains or regions that have an affinity for the other of the receptor or target. As used herein, "hybridization" refers to the use of complementary single-stranded polynucleotides as both the target and the receptor wherein at least a portion of the target polynucleotide is complementary to at least a portion of the receptor polynucleotide. Chemical interactions can include, but are not limited to, covalent bonding, ionic bonding, hydrogen bonding, van der Waals forces, or the like, between the target and the receptor.

Any recognition interaction complex, comprising two or more components, can be used for the capture molecule/target analyte in the biosensor arrays and instruments of the present invention. These include, but are not limited to, interactive pairs (e.g., protein:protein, protein: ligand, protein: lipid, protein: carbohydrate, protein: drug, polynucleotide: polynucleotide, polynucleotide:protein, polynucleotide: ligand, polynucleotide:drug, antibody:antigen, or the like), interactive triplets, or interactive multiplets (e.g., a multiprotein complex).

Use of the phrase "polynucleotide" is intended to encompass DNA and RNA, whether isolated from a virus, bacterium, plant, or animal (e.g., mammal), or synthetic; whether single-stranded or double-stranded; whether including naturally or non-naturally occurring nucleotides; or chemically modified. As used herein, "polynucleotides" also encompass single or multiple stranded configurations, where one or more of the strands may or may not be completely aligned with another (e.g., partial hybridization, stem loops, or the like). The terms "polynucleotide" and "oligonucleotide" shall be generic to polydeoxynucleotides, to polyribonucleotides, to any other type of polynucleotide which is an N-glycoside of a purine or pyrimidine base, and to other polymers in which the conventional backbone has been replaced with a non-naturally occurring or synthetic backbone or in which one or more of the conventional bases has been replaced with a non-naturally occurring or synthetic base. An "oligonucleotide" generally refers to a nucleotide multimer of about 2 to 100 nucleotides in length, while a "polynucleotide" includes a nucleotide multimer having any number of nucleotides greater than 1, although they are often used interchangeably.

The receptor and/or the target analyte can be chosen from, but is not limited to, an analyte or chemical, such as that found in an organism (e.g., a virus, bacterium, yeast, animal, human, plant, or the like), a carbohydrate, a peptide, a protein, a lipid, a nucleic acid, a hormone, a vitamin, a co-factor, a drug, a small molecule, or the like. The target can be in the form of an ion to facilitate the interaction between itself and the probe.

As stated above, the biosensor array includes two or more microelectrodes, such as the one shown in FIG. 1 and described immediately above. In this manner, the electrochemical biosensor array can be advantageously used to conduct multiple analyses simultaneously. This feature, not only provides significant time-savings, but, when implemented in a bench-top or portable instrument, also enables on-site, higher-throughput or combinatorial screening. In making an array, multiple microelectrodes are produced on the substrate. The multiple microelectrodes can be produced sequentially, in groups, or simultaneously.

Figure 3:
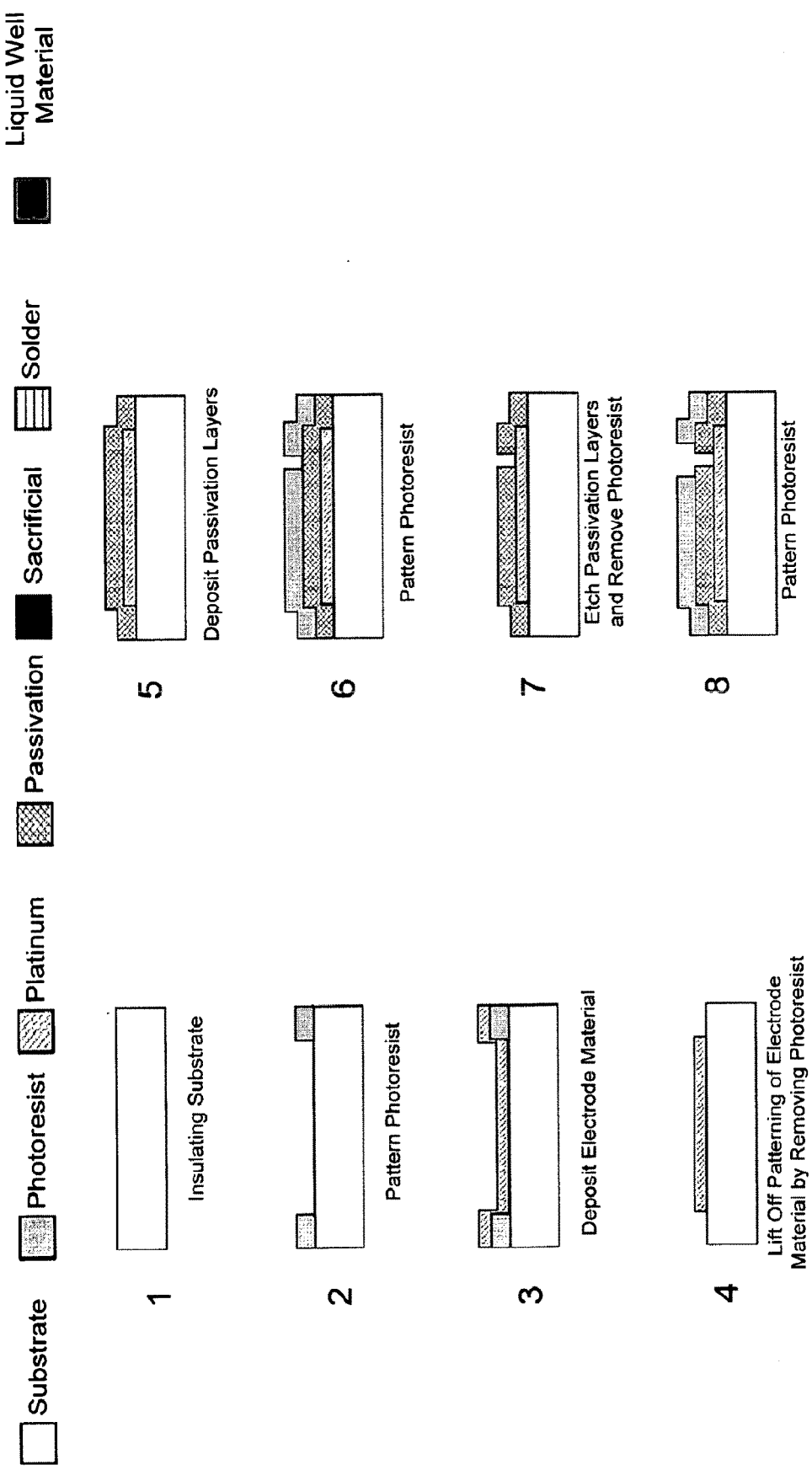
FIG. 3 schematically illustrates a method for making a biosensor array having a plurality of microelectrodes simultaneously according to some embodiments of the present invention.

FIG. 3 provides an exemplary method for making a biosensor array having a plurality of microelectrodes, wherein the array of microelectrodes is made simultaneously. It should be recognized that not all of the process steps described in relation to FIG. 3 will be necessary to prepare the biosensor arrays according to the various embodiments of the present invention. In fact, other than the deposition of the electrode support and connection points, each subsequent step shown in FIG. 3 is an optional step that can provide additional beneficial features to the biosensor arrays of the present invention as will be recognizable to those skilled in the art to which this disclosure pertains.

The process generally begins with the selection or provision of the electrically insulating substrate. The electrode supports, along with the points for connections to outside (i.e., not on the substrate) components for each electrode support, are then disposed in a pattern, which corresponds to the shape and size of each of the locations of the microelectrodes and the connection points (i.e., contact pads), upon at least a portion of the surface of the substrate. This can be accomplished, for example, by patterning the substrate with a mask, followed by deposition of a layer of the electrode support directly on at least the exposed portions in the patterned mask. The mask can be deposited using any known method for creating a mask (or a photoresist or photomask) on a substrate, such as by photolithography, photoengraving, or the like. Similarly, the electrode support can be deposited using any known thin film deposition technique, such as chemical vapor deposition (e.g., low pressure deposition, ambient pressure deposition, plasma-enhanced deposition, microwave-enhanced deposition, atomic layer deposition, metal-organic deposition, vapor phase epitaxial deposition, or the like), physical vapor deposition (e.g., pulsed laser deposition, sputtering, arc deposition, electron beam deposition, evaporative deposition, or the like), or the like.

In the process shown in FIG. 3, a photoresist is patterned on the substrate, followed by sputtering of the electrode support and connection points. Subsequently, the photoresist is removed to leave only the patterned electrode support and connection points. That is, the sputtered material that was not deposited in the openings of the photoresist was lifted off by removal of the photoresist. Removal of the photoresist (and any material coated thereon) can be performed using any known method for removing a photoresist. For example, the photoresist can simply be washed away by using a solvent that removes only the photoresist.

Once the electrode supports and connection points have been placed on the substrate, a passivation layer can be formed. The electrode support for each microelectrode is electrically connected to its respective connection point. Regardless of the distance between the electrode support and the connection point for each microelectrode, the electrical connection therebetween can be subjected to various processing and operating conditions that can deteriorate it over time. In addition, the electrode support and the connection point for each microelectrode can be can be subjected to various processing and operating conditions that can deteriorate it over time. Thus, a passivation layer can be used to insure against situations where deterioration of the electrode supports, connection points, and the regions in between can occur.

The passivation layer should be sufficiently insulating to prevent electrical communication between the deposited components of nearby microelectrodes. Thus, the passivation layer can be formed from any electrically insulating material, such as those materials already described above for the substrate. In exemplary embodiments, the passivation layer is formed from silicon dioxide or silicon nitride.

The passivation layer can be deposited on at least the portion in between the electrode support and the connection point for each microelectrode. This can also include deposition on one or both of the electrode support and the connection point for each microelectrode, depending on the subsequent processing or operating conditions to be protected against. Deposition of the passivation layer can be accomplished using any known thin film deposition technique, such as those described above for deposition of the electrode support and connection points. In the process shown in FIG. 3, the passivation layer is deposited using chemical vapor deposition over the entire substrate (including the patterned electrode support and connection points).

Once the passivation layer has been deposited to protect the selected regions of the deposited coating, any exposed regions can be subjected to further processing. In the process shown in FIG. 3, the entire substrate was coated with the passivation layer. Thus, a portion of the passivation layer is removed. This is achieved by patterning a second photoresist over the passivation layer, and subjecting the openings in this photoresist to an etching process. The etching process, which includes dry etching or chemical etching, serves to remove the exposed passivation layer to allow the regions underneath to be subjected to further processing. Once the passivation layer has been etched, the second photoresist can be removed as well.

While either the portion of the passivation layer over the electrode support or the portion over the connection points can be removed first, the process in FIG. 3 illustrates the former route. These exposed regions in the passivation layer will serve as the regions onto which the polymer bilayer is ultimately disposed. The average longest dimension of the exposed region here can vary from about 5 micrometers to about 50 micrometers. In FIG. 3, this is shown as a circle for convenience, but any shape region (e.g., square, rectangle, trapezoid, hexagon, or the like) can be used. When larger exposed regions are used, the production costs are lower, and the possibility for internal resistance, current loss, and noise are minimized. When smaller exposed regions are used, a greater number of microelectrodes can be created on a single substrate, which can result in a larger data sample for a single analysis. In exemplary embodiments, the exposed regions are circular and have an average diameter of about 20 micrometers.

Once the electrode support for each microelectrode of the biosensor array has been prepared for the polymer bilayer to be disposed thereon, the connection points can be prepared for being connected to any outside components. This can be accomplished by adding a solder layer to the connection points. If there is any passivation layer over the connection points, it should be removed first.

If, however, additional processing is desired, additional steps can be undertaken before preparing the connection points for being connected to outside components. For example, if the individual microelectrodes are to be isolated from one another, such as by the creation of a physical barrier or wall between each microelectrode, such walls can be created at this time. As will be described below, there can be advantages (e.g., ease of preparing microelectrodes that have different probes) to isolating the individual microelectrodes from one another.

In fabricating walls between individual microelectrodes, it may be desirable to first protect the exposed regions of the electrode support. Thus, a sacrificial protective layer can be disposed on the exposed regions of the electrode support. The only limitation on the properties of the material used to form the sacrificial protective layer is that it has to withstand any subsequent processing conditions to which it is exposed (prior to being removed in order to deposit the polymeric bilayer on the exposed region it has protected). In exemplary embodiments, the sacrificial protective layer is formed from a metal or polymer.

The sacrificial protective layer can be deposited on the exposed regions of the electrode support using any known thin film deposition technique, such as those described above for the deposition of the electrode support and connection points.

In the process shown in FIG. 3, a third photoresist is patterned on the substrate to control where the sacrificial protective layer will be deposited. Subsequently, the sacrificial protective layer is sputtered over the entire substrate (including the third photoresist and the exposed regions). After deposition of the sacrificial protective layer, the photoresist is removed, and only the previously exposed regions are coated with the sacrificial protective layer.

Once the exposed regions have been protected, the barrier walls between each microelectrode can be prepared. These can be fabricated, for example, by photolithographic patterning (e.g., using a photo-curable material such as an epoxy) or by shadow masking. In the process shown in FIG. 3, the walls are patterned photolithographically. The height of the walls can be less than or equal to about 200 micrometers. For greater isolation, it may be desirable for the height of the walls to be greater than or equal to about 100 micrometers.

In certain situations, it may be beneficial to further create barriers between groups of isolated microelectrodes. When using a multi-microelectrode array, each microelectrode can be different such that it is activated by only one target. Alternatively, two or more microelectrodes can be identical, with the same target activating each of the identical microelectrodes. The number of microelectrodes that are activated by the same specific target can vary from array to array, and can be selected by the user for a particular application. Generally, an array containing several identical microelectrodes that can be activated by the same target yields redundant information, which can enhance the statistical accuracy of the analysis. Thus, in these instances, it may be beneficial to have a significant number of identical microelectrodes within a given array.

When an array has multiple identical microelectrodes, the array can be divided into groups of microelectrodes. That is, a barrier can be created between groups of identical microelectrodes. In the process shown in FIG. 3, this division takes place in the form of a wall that is higher between the groups than between the isolated identical microelectrodes of a given group. The so-called "group walls" are simply patterned to a height that is two or more times that of the walls that isolate the individual microelectrodes of the group.

Once any desired barriers are fabricated between the individual, or groups of, microelectrodes, the connection points can be prepared for being connected to outside components. As stated above, this can be accomplished by adding a solder layer to the connection points. Again, if there is any passivation layer over the connection points, it should be removed first. In the process shown in FIG. 3, this is accomplished by patterning a fourth photoresist such that the openings in this photoresist correspond to the passivation layer covering the connection points. The passivation layer is then etched away.

The exposed connection points can then have the solder layer deposited thereon. The solder layer should be thin enough such that there is no interconnection of connection points, but thick enough to allow a proper bond to be formed between the biosensor array and the outside components. In some circumstances it may be desirable to deposit the solder layer as two separate coatings. For example, a first seed layer could be deposited on the connection points followed by a second, thicker layer. In this manner a stronger bond between the connection point and the solder layer can be formed. The seed layer can be deposited using any of the thin film deposition techniques described above, while the second solder layer can be electroplated thereon. In the process shown in FIG. 3, the solder layer is deposited in one step, as a single layer over the entire substrate (which includes the fourth photoresist and the exposed regions of the connection points).

Once the solder layer has been prepared, the biosensor array is ready to be connected to any outside components. That is, the biosensor array can be used to form a biosensor instrument. In the process shown in FIG. 3, the fourth photoresist needs to be removed before this is done.

Figure 4:
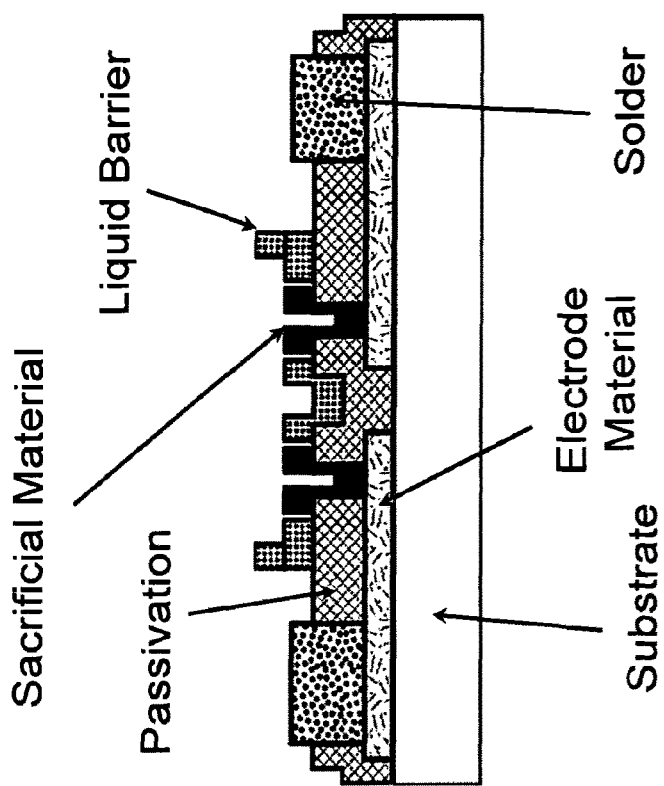
FIG. 4 schematically illustrates a biosensor array having 16 microelectrodes according to some embodiments of the present invention.
Figure 4:
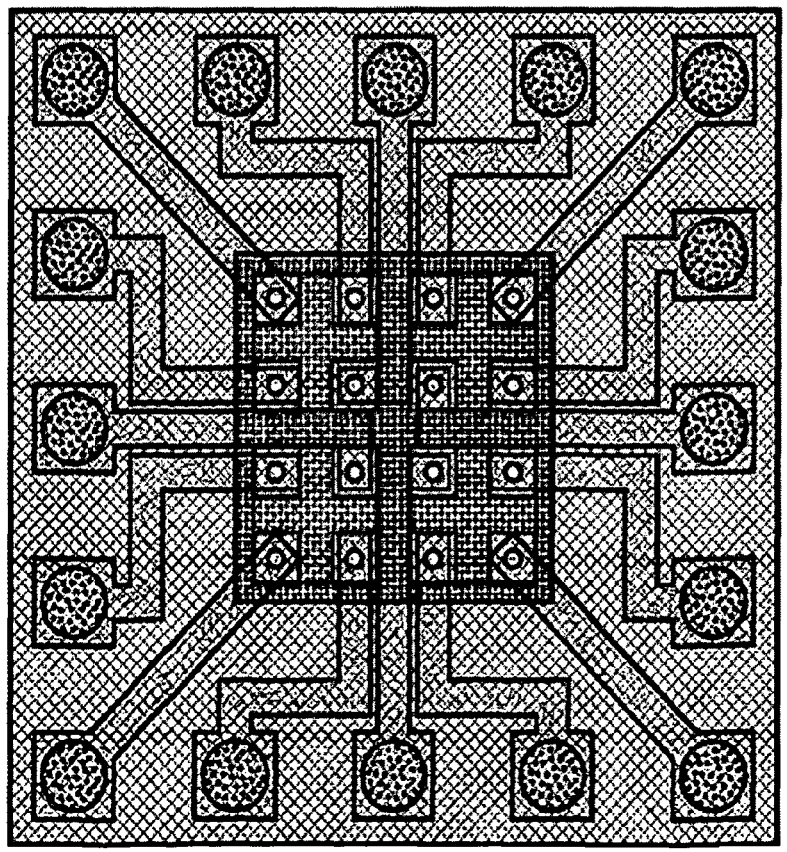
Figure 5:
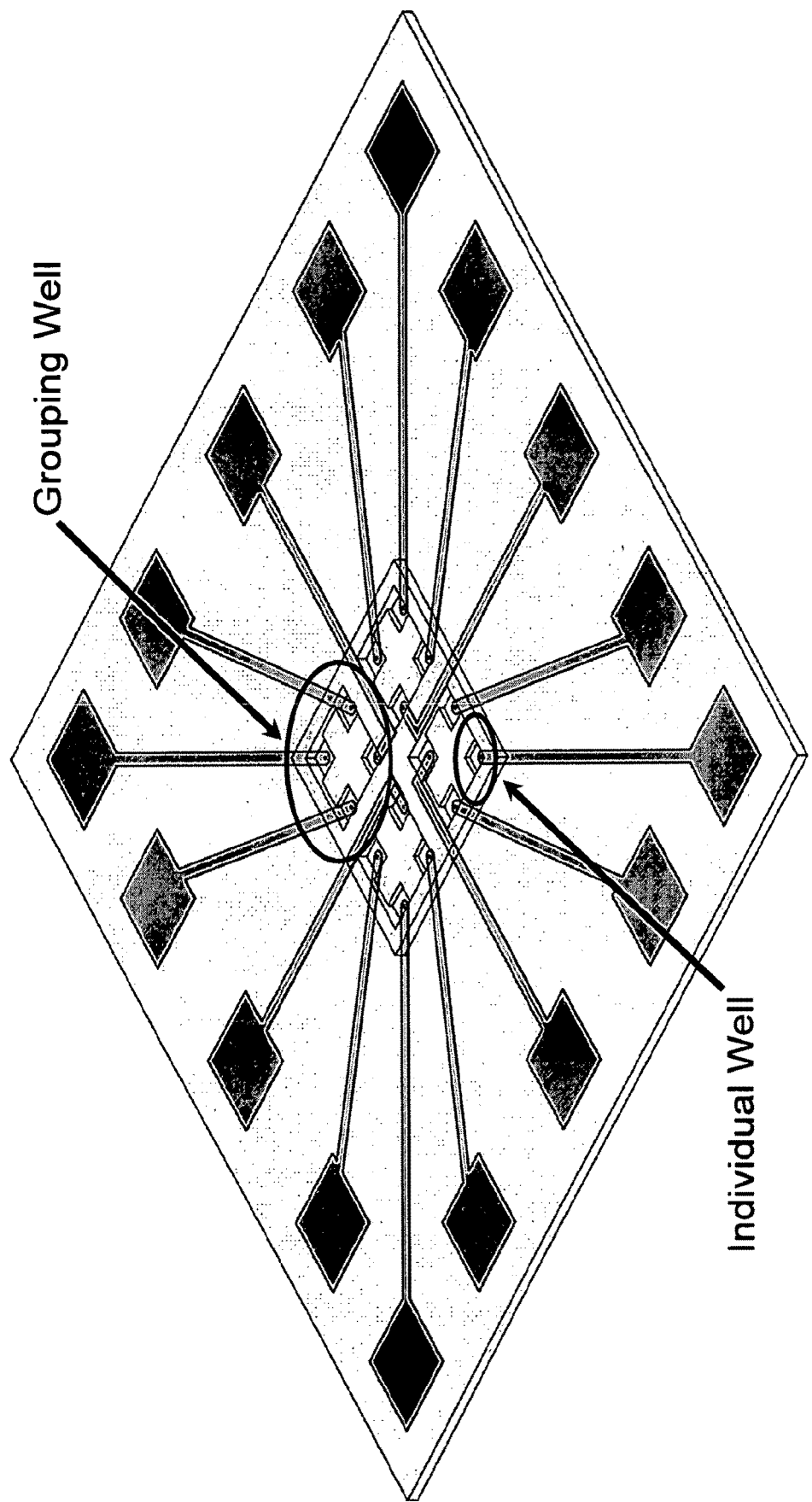
FIG. 5 schematically illustrates a biosensor array having 16 microelectrodes according to some embodiments of the present invention.

FIGS. 4 and 5 provide schematic illustrations of biosensor arrays produced according to the various embodiments of the present invention. More specifically, FIG. 4 illustrates top and side views of a biosensor array having 16 microelectrodes prepared using each of the process steps shown in FIG. 3 and described above. The shading of the components in FIG. 4 matches that of FIG. 3 for illustrative convenience. The biosensor array shown in FIG. 5 provides a perspective view of a similar 16 microelectrode array, with more emphasis on the barrier walls used to isolate individual microelectrodes as well as groups of four microelectrodes, and less emphasis on processing conditions.

While FIGS. 4 and 5 depict biosensor arrays having 16 electrodes, there is no specific limit to the number of microelectrodes in a particular array, other than the physical constraints of the substrate. For manufacturing and data processing convenience, it is desirable to limit the number of microelectrodes in a biosensor array to less than or equal to about 128 individual microelectrodes. In exemplary embodiments, the biosensor arrays include about 8 to about 32 microelectrodes.

Similarly, while FIGS. 4 and 5 depict biosensor arrays with the microelectrodes located in the center of the array and the connection points on the outside edges of the substrate, there is no particular limitation to the geometry and/or the layout of the biosensor arrays. For manufacturing convenience, it may be desirable to aggregate all of the microelectrodes or connection points in one location, but this is not necessary.

It should be recognized by those skilled in the art to which this disclosure pertains that it is possible for multiple biosensor arrays to be fabricated using a single substrate. These biosensor arrays should be separated from one another by breaking down the substrate into the individual biosensor arrays before fabricating a biosensor instrument.

Referring again to FIG. 2, an exemplary biosensor instrument includes a biosensor array and one or more of a temperature control mechanism, a fluid control mechanism, additional instrumentation for the biosensor array, and a signal processing mechanism. When more than one of these components are implemented, they can independently be in operative communication with one or more of the other components.

In forming the biosensor instrument, the first outside component to which the biosensor array is connected is generally a printed circuit board that contains signal processing circuitry to couple the biosensor array to at least the signal processing medium. Before connecting the biosensor array to the printed circuit board, however, the biosensor array can be cleaned to ensure that no contaminants or debris from the biosensor array processing steps remain thereon. This can be accomplished using a wet cleaning process (e.g., with a chemical solution and/or deionized water) or a dry cleaning process (e.g., with gases and/or plasma etching).

Figure 6:
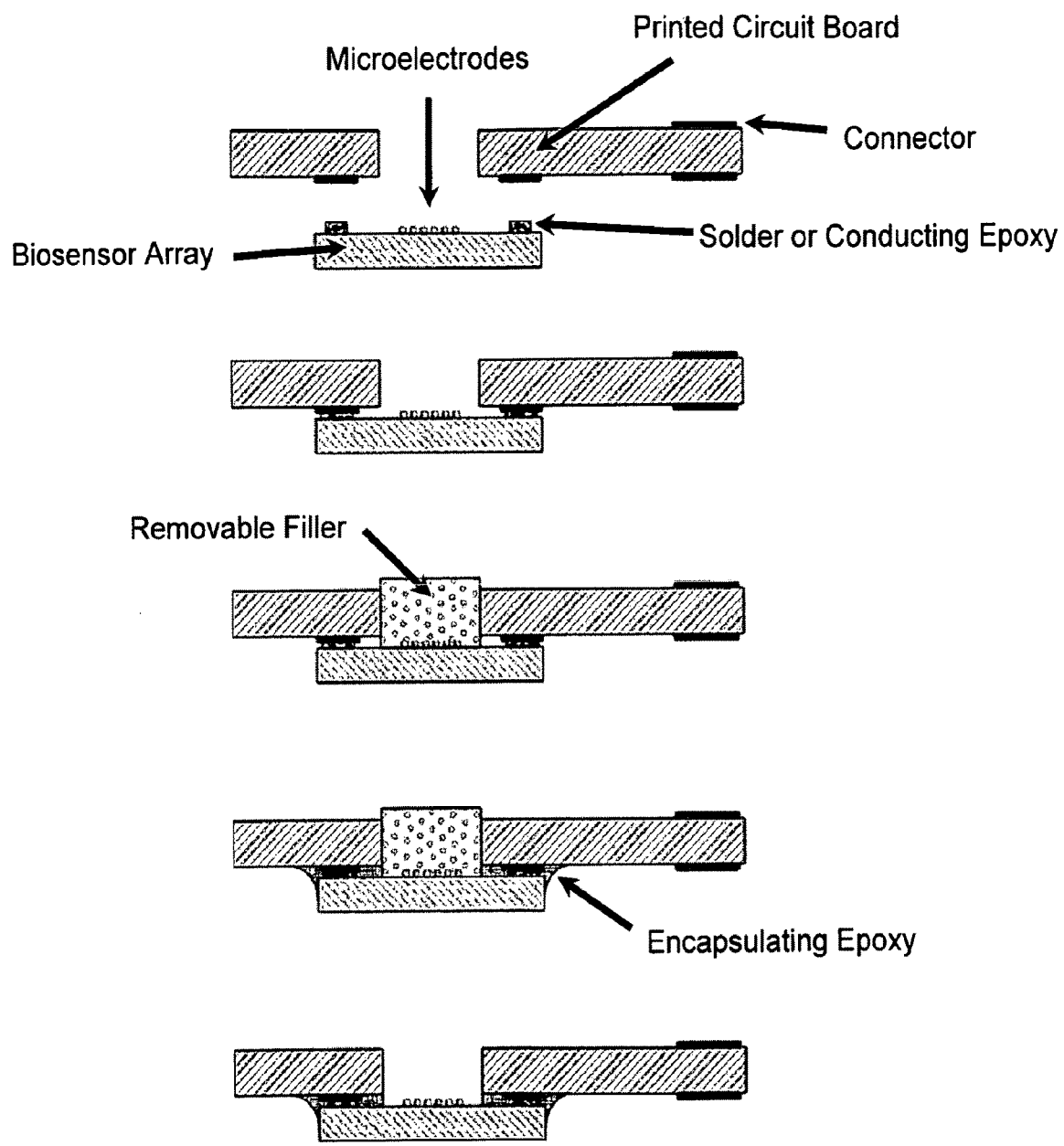
FIG. 6 schematically illustrates a method for connecting a biosensor array to the signal processing circuitry of a printed circuit board according to some embodiments of the present invention.

An exemplary process for connecting a biosensor array to a printed circuit board is shown in FIG. 6. As indicated in the figure, the biosensor array is connected to the printed circuit board in a manner that essentially creates a reaction vessel or solution well for easier operation of the biosensor instrument. This connection can be formed between the biosensor array and two separate printed circuit boards, that together have the requisite signal processing circuitry, or between the biosensor array and a single printed circuit board with a via formed therein. In situations where the biosensor array is connected at a via, the via can have a coating on its vertical wall so as to prevent possible damage from any of the chemical solutions used to prepare the biosensor instrument or during operation of the instrument.

The printed circuit board can have connection points (i.e., contact pads) that correspond in number to those of the biosensor array. The respective connection points can be bound together by wire bonding, solder bump bonding, or tape automated bonding, all of which are techniques known to those skilled in the art to which this disclosure pertains. In the process shown in FIG. 6, the biosensor array is connected to the printed circuit board using solder bump bonding of the self-aligning connection points.

In some situations, once the connection points have been bound together, the connection can be further improved or strengthened by a seal that is formed, for example, using an underfill system or an encapsulation system. In the process shown in FIG. 6, an underfill system is used. The seal is formed by filling the reaction vessel or solution well with a removable material (e.g., a gel, gum base, shaped plastic article, or the like), and placing a non-conductive adhesive underfill material, which is frequently an epoxy, in the open spaces between the biosensor array and the printed circuit board. Once the seal has been formed, the removable material is removed from the reaction vessel or solution well. The connection process is now complete.

The connected biosensor array and printed circuit board package can then be connected with any other component of the biosensor instrument, such as those shown in FIG. 2 and described in further detail below.

In some embodiments, in addition to the biosensor array/printed circuit board package, the biosensor instrument also includes a reference and counter/auxiliary electrode. There can be one reference and counter/auxiliary electrode for each microelectrode in the biosensor array; or there can be one common reference and counter/auxiliary electrode for more than one, or all, of the microelectrodes in the biosensor array. The reference and counter/auxiliary electrodes can be made of various conductive materials, as discussed above for the electrode supports of the microelectrodes.

The various electrodes can be in operative communication with an electrochemical workstation that provides a current or voltage source to the three electrode cell. This provides a flow of electrons to the three-electrode cell(s) that is monitored and measured at the workstation by a signal processing mechanism, which reports and records the voltammetric current. The voltammetric current, and changes therein, can be recorded as a cyclic voltammogram. The workstation may provide a voltage source to the electrode and measure a current, but it is also capable of working in reverse providing a current source and measuring a voltage. Either set-up is acceptable for operating the biosensor instruments of the present invention.

The signal processing mechanism can be a personal computer, mainframe, portable computer, personal data assistant, or the like. The signal processing mechanism can include data transfer and evaluation protocol capable of transforming raw data from the biosensor array into information regarding the presence, absence, and the extent of the interaction of a target analyte. The signal processing mechanism can also be capable of providing diagnostic information regarding the target analyte.

Generally, the solid state electronics, including, for example, a potentiostat circuit connected to working and reference electrodes, as described above for performing electrochemical measurements, are external to the biosensor array/printed circuit board package. Notwithstanding this, the biosensor array/printed circuit board package, reference and counter/auxiliary electrodes, electrochemical workstation, and signal processing mechanism can be arranged in a variety of configurations, when in combination with other components that are known to those of skill in the art.

By way of example, one such component is a temperature control mechanism.

Figure 7:
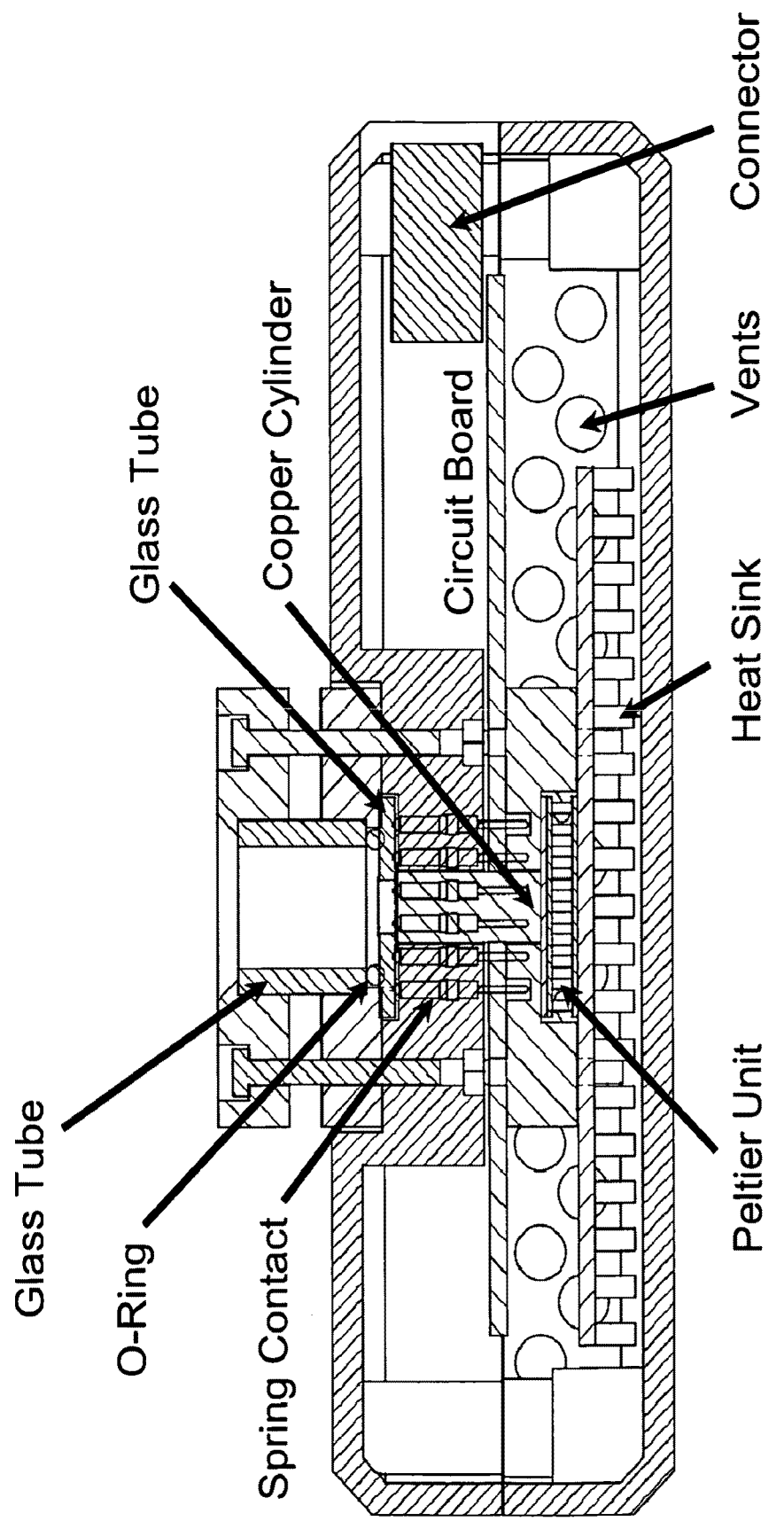
FIG. 7 schematically illustrates a biosensor instrument having temperature-regulating capabilities according to some embodiments of the present invention.
Figure 8:
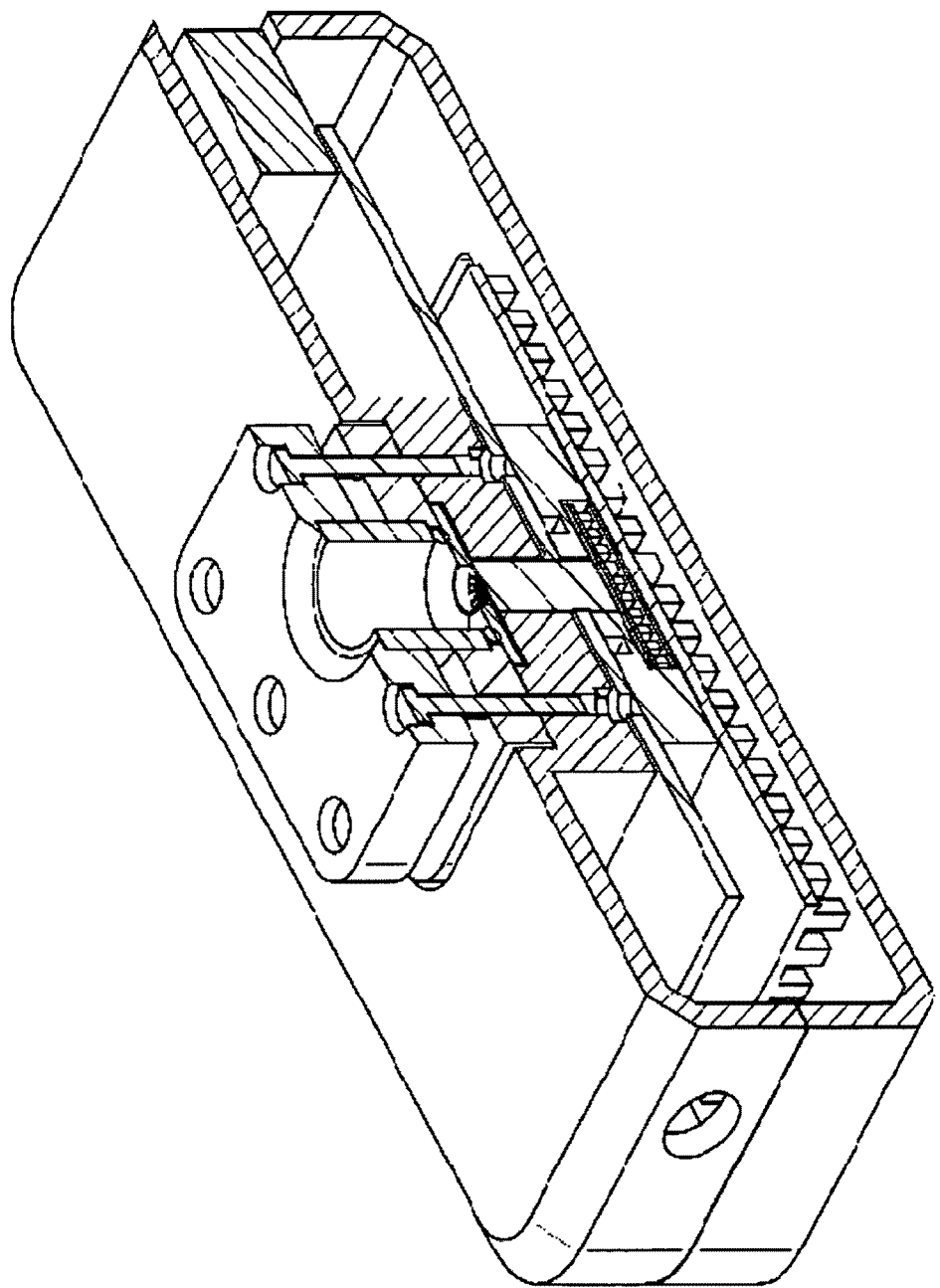
FIG. 8 schematically illustrates a biosensor instrument having temperature-regulating capabilities according to some embodiments of the present invention.

The biosensor instrument can include a cooling/heating feature to enable temperature-dependent signal acquisition and a passivation capability to allow electrolyte exposure only to the microelectrode array portion of the chip. Schematic illustrations of different perspectives of a cross-section of an exemplary system having temperature-regulating capabilities are included in FIGS. 7 and 8. As emphasized in FIG. 8, the system can make use of vents, heat sinks, thermoelectrics (i.e., Peltier units), thermal conductors (e.g., copper), and the like, to control the temperature. Accordingly, the overall electrochemical biosensor system has so-called "push-pull" control capabilities. That is, heat can readily be added (i.e., pushed) to, or removed (i.e., pulled) from, the system by taking advantage of one or more of these various optional components. For example, in biosensor instrument having a feedback control loop and a temperature sensor (e.g., a thermocouple, thermistor, or the like), the temperature can be adjusted either positively or negatively to compensate for any deviation from the intended temperature during signal acquisition. Alternatively, the temperature can simply be adjusted according to a desired temperature profile during the signal acquisition process. Thus, it is possible to take measurements at variable temperatures for a particular analyte or analytes.

The biosensor instrument can also include a fluid control mechanism to control the delivery and removal of fluid to and from the biosensor array. Such a feature enables greater precision in analyte solution delivery, thereby minimizing the concerns for cross-contamination of microelectrodes. As a result, a greater number of samples can be analyzed correctly during a given trial.

Either before or after the biosensor array/printed circuit board package is connected with the other biosensor instrument components, at least a portion of the remainder of the microelectrodes' components (the polymeric bilayer, multivalent metal cation, and receptor) can be formed as described above in reference to FIG. 1.

In order to deposit the polymeric bilayer on the electrode supports, however, the sacrificial protective layer of each microelectrode, if used, must be removed. Removal of the sacrificial layer can be accomplished by its dissolution in an appropriate etching solution. By way of example, if aluminum is used to form the sacrificial protective layer, then it can be removed by dilute hydrochloric acid or by commercial aluminum etchant. Once this layer has been removed, at least the polymeric bilayer can be disposed on the electrode supports.

In some situations, it may be desirable to perform an electrochemical cleaning of the exposed portion of the electrode support before disposing the polymeric bilayer no the electrode support. The electrochemical cleaning, which serves to remove any residual impurities on the surface of the electrode support, can be accomplished using electrolysis.

In preparing the individual microelectrodes for use, the bilayer should be deposited as uniformly as possible. Particularly when there are individual and group barriers between microelectrodes, an electropolymerization technique using programmed potential/time sequences is desirable for depositing the uniform layer of a conducting polymer within the recesses. The voltage of the pulses can be less than or equal to about 1 Volt, with less than or equal to about 800 milliVolts preferred. Each pulse can last about 5 milliseconds to about 20 milliseconds, with an interval of about 5 seconds to about 15 seconds between potential pulses. The optimum bilayer deposition procedure will depend on the geometry of the recessed channels and can readily be determined by one of skill in the art without undue experimentation. For example, in depositing the bilayer in the channels of a 16-channel array similar to that shown in FIG. 5, a potential was applied for about 10 milliseconds at a voltage of about 800 mV, followed by a series of shorter pulses each separated by several seconds.

Figure 9:
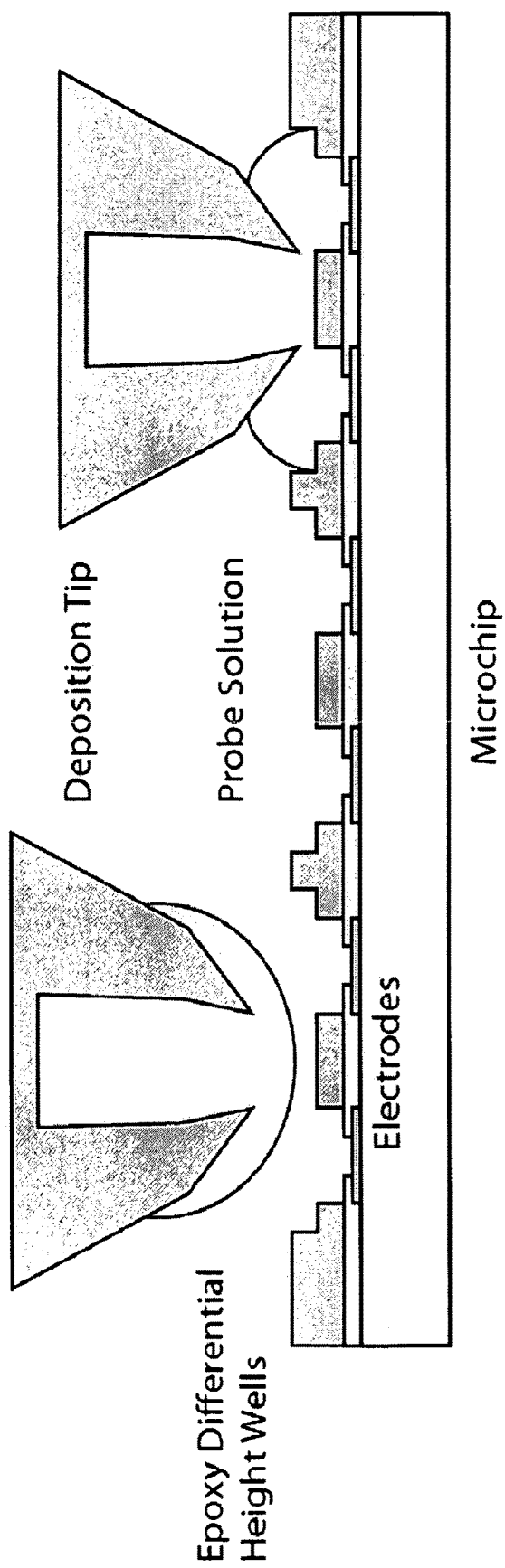
FIG. 9 schematically illustrates a biosensor array with two groups of identical microelectrodes that independently have different probes and have the same probe within the group according to some embodiments of the present invention.

After the bilayer has been prepared, it can be contacted with a solution containing a multivalent metal cation in order to form a salt for complexing the probe and/or contacted with a solution containing the probe in order to bind the probe to the bilayer. If the entire array is to contain the same probe, then it can be exposed to the probe-containing solution at once. If there are groups of microelectrodes that will each have a unique probe, the groups will be exposed to different solutions. The variable height of the group barriers facilitates deposition of the probes within each group of identical microelectrodes and minimizes the risk of cross-contamination between groups. FIG. 9 depicts an array having groups of identical microelectrodes, wherein each group of microelectrodes includes a different probe, but wherein each of the channels of a particular group has the same probe.

In some embodiments, the biosensor array can be packaged with the bilayer disposed on the electrode support material, but without the probe or probes attached. Arrays and instruments fabricated this way can be stored for prolonged period of time before use. These arrays and instruments can then be transformed into an active diagnostic mode either on-site or off-site, on an "as needed basis" by exposure to the solution of the probe or probes.

Other embodiments of the invention are directed to methods of using the biosensor instruments to detect a target analyte in a sample to be analyzed. The biosensor instruments are made according to the methods described above with an array of working microelectrodes having polymeric bilayers coating thereon, and capture molecules attached thereto. In some embodiments, each microelectrode in the array has the same capture molecule, and in other embodiments one or more of the microelectrodes may have different capture molecules than one or more of the other microelectrodes, thereby enabling the biosensor to detect more than one different target analyte in a sample simultaneously.

Again, the biosensor instrument also includes signal processing circuitry, as discussed above. The electrode is then contacted with a sample to be analyzed (e.g., in sufficient contact with the sample for a target analyte contained in the sample to interact with the capture biomolecule), and the system is interrogated using standard electrochemical techniques. As discussed above, the biosensor instrument includes a current source to provide a flow of electrons to drive the electrochemical processes at the microelectrode and a signal processing mechanism for detecting and reporting any change at the electrode. As discussed above, some embodiments of the biosensor system also include a data analysis component (e.g., data analysis software on a computer system coupled to the biosensor array described above) for storing and evaluating the electrochemical signal produced by the biosensor-chip array.

In exemplary embodiments, a cyclic voltammogram is recorded in an ion-containing buffer individually for every microelectrode of the biosensor array and stored in the computer memory (e.g., as matrix A). For this step a common auxiliary electrode and common reference electrodes can be used. For the recognition interaction event, the sample solution can be applied to the biosensor array for about two minutes to about 30 minutes. The interaction event takes place according to the degree of affinity of the target for the probe. The array can then be rinsed in the same buffer, individual electrochemical measurements can be performed again, and the results can be stored in the computer memory (e.g., as matrix B).

With the biosensor arrays of the present invention, this process can be performed on a platform that accommodates numerous microelectrodes. Then, diagnostic information can be obtained from the collective response of the array (multivariate analysis), involving all elements of the array or, optionally, only a selected number of array elements.

In exemplary embodiments, the instrument accommodates the targeted electrode in every microelectrode of the array and is thus able to conduct the voltammetric measurements in a microelectrode format. In such embodiments, the counter electrode and the reference electrode, which form part of an electrical circuit, can be common. In some embodiments, an array of readout electronics is connected to an array of counter electrodes to record electric current through such array of counter electrodes. The system also preferably includes a dedicated electronic circuit that can collect the voltammetric data in digital form for the electrochemical measurement.

In exemplary embodiments, the data analysis component/software has the ability to create difference voltammograms (e.g., by subtraction of matrices B and A described above to create a matrix C). The data analysis component can have the ability to integrate the current in matrices A and B, thus forming charge matrices A' and B', and to subtract them to create matrix C'. This component can also have the ability to record the time evolution of matrix C and C'. The data analysis component can include shape recognition analysis, allowing training using all available parameters, namely C and C' and their time evolution matrices. The information can be enhanced by using temperature-dependent/variable measurements and the respective signal differences. The data analysis component can also present the results in simple diagnostic terms and provide authenticated access to raw electrochemical data.

The shape or pattern recognition software can be manipulated to extract information that is contained in specific parts of the voltammograms. The software can also maintain and combine data obtained at different temperatures and/or using different combinations of probes. Advantageously, an increased recognition capacity can be achieved by using the various experimental parameters and the results collected therefrom.

Those skilled in the art to which this disclosure pertains will also appreciate that the sensing portion of the biosensor instrument (e.g., the biosensor array/printed circuit board package) is reusable. The bound target analyte can be removed and the sensor reused to detect the same analyte in a different sample. Alternatively, the capture molecule can also be easily removed, and a new capture molecule added to use the biosensor instrument for detecting a different analyte. Those of skill in the art will also understand that the biosensor of the present disclosure, prepared in an array format, can be adapted to detect many different analytes and used for high throughput applications.

In other embodiments, instead of reusing the sensing portion, a disposable sensing portion can be implemented. The biosensor array/printed circuit board package preferably does not contain any CMOS-type circuitry. In this manner, the biosensor array/printed circuit board package can be fabricated rather inexpensively and/or using non-sophisticated fabrication techniques. When using a disposable package, the number of available microelectrodes can be smaller than on a non-disposable package, allowing for greater ease in manual deposition of the probes. Advantageously, such an instrument, including the disposable package, is aimed at low cost, bench top, or field applications. It should be noted that the embodiments shown in FIGS. 4, 5, 7, and 8, can also be implemented as disposable devices, in addition to being implemented as non-disposable and/or reusable devices.

Figure 10:
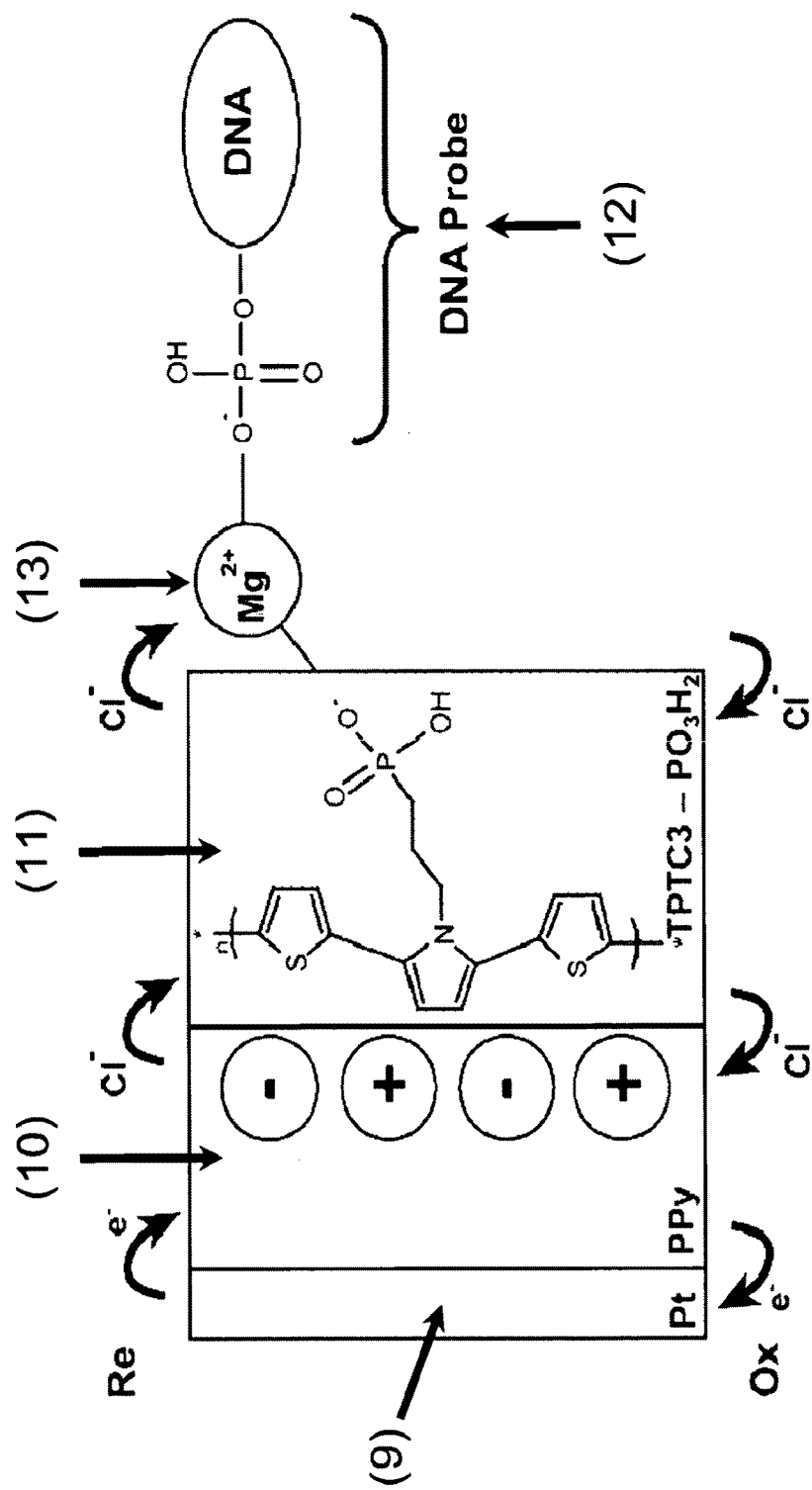
FIG. 10 schematically illustrates a microelectrode of a biosensor array according to some embodiments of the present invention.

By way of example, reference will now be made to a biosensor array and instrument where the probe is a single stranded DNA. FIG. 10 illustrates a microelectrode for such an array and instrument. The electrode support was formed from platinum, the first polymer layer was formed from polypyrrole, and the second polymer layer was formed from a monolayer of pTPT. The pendant phosphonate group of the pTPT was complexed with a magnesium ion to form a pTPT-MgCl complex salt. The complex salt was contacted with a single stranded DNA probe having a phosphate group attached thereto, to form a pTPT-Mg-ssDNA complex. Additional information can be found in L. A. Thompson, J. Kowalik, M. Josowicz and J. Janata, J. Am. Chem. Soc., 125 (2003) 324-325, "Label-free DNA Hybridization Sensor Based on a Conducting Polymer"; and Temitope Aiyejorun, Liz Thompson, Janusz Kowalik, Mira Josowicz and Jiri Janata, Control of Chloride Ion Exchange by DNA Hybridization at Polypyrrole Electrode, Electrochemistry of Nucleic Acids and Proteins, E. Palecek, F. Scheller and J. Wang, Eds., Elsevier Publishers (2005), 331-344, which are incorporated by reference herein in their entireties as if fully set forth below.

It should be noted that when the target analyte is DNA, DNA hybridization can be improved by using protein ribonucleic acid (PNA) as the capture molecule. PNA can be used in addition to, or instead of, DNA. One advantageous feature of using PNA is that, unlike DNA or RNA, PNA does not have the negative charge associated with phosphates. Consequently, positive identification of hybridization relies on detecting the difference between the uncharged and negatively charged state of the electrode.

It should also be noted that a programmable temperature profile can be quite beneficial for direct (i.e., single-step) detection of very large genomic DNA fragments, such as those containing up to 20,000 bases or more. The melting temperature increases with number of base-pairs in the duplex. In order to achieve direct hybridization detection, without PCR amplification or separation of the target DNA, it is necessary to disassociate (i.e., melt) the native duplex, so that the single-stranded DNA can hybridize with the probe immobilized at the electrode. The time required for re-hybridization generally increases with the number of bases. Thus, a sample containing genomic DNA can be externally heated, for example, to a temperature of about 94° C. to about 98° C. in an appropriate buffer. The heated sample is then allowed to cool down to a certain temperature at which point it is presented to the electrode with the immobilized probe. The choice of this re-hybridization temperature is another means of increasing the selectivity. When probes having different numbers of bases are used in different channels (e.g., as described above and shown in FIGS. 8 and 9), the longer probes re-hybridize and are detected first. Thus the choice of insertion or re-hybridization temperature is linked to the length of the selected probes. The preferred temperature ranges for this process are about 40° C. to about 70° C. For example, one probe can re-hybridize at about 65° C. to about 70° C., while another re-hybridizes at about 60° C. to about 65° C., while still another re-hybridizes at about 55° C. to about 60° C., and so on, until all probes that can be re-hybridized are, in fact, re-hybridized.

Although the present embodiments have been described with reference to cyclic voltammetry, various electrochemical techniques can be employed in such a system including, but not limited to, various forms of voltammetry, impedance and amperometry, such as cyclic voltammetry, AC voltammetry, AC impedance, square wave voltammetry and differential pulse voltammetry. Most of the above techniques may all be applied with the same electrochemical set up, but with different characteristics to the applied and measured voltages and currents. Any differences to the electrochemical set up that would be required to implement a different electrochemical technique would be understood by those of skill in the art and are intended to be included in the scope of the disclosure.

The embodiments of the present invention are not limited to the particular formulations, process steps, and materials disclosed herein as such formulations, process steps, and materials may vary somewhat. Moreover, the terminology employed herein is used for the purpose of describing exemplary embodiments only and the terminology is not intended to be limiting since the scope of the various embodiments of the present invention will be limited only by the appended claims and equivalents thereof. For example, temperature and pressure parameters may vary depending on the particular materials used.

Therefore, while embodiments of this disclosure have been described in detail with particular reference to exemplary embodiments, those skilled in the art will understand that variations and modifications can be effected within the scope of the disclosure as defined in the appended claims. Accordingly, the scope of the various embodiments of the present invention should not be limited to the above discussed embodiments, and should only be defined by the following claims and all equivalents.

What is claimed is:

1. An electrochemical biosensor array, comprising: an array of microelectrodes disposed on a substrate, wherein each microelectrode comprises: a conducting electrode material disposed on a portion of the substrate; a first polymeric layer disposed on at least a portion of the conducting electrode material; a second polymeric layer disposed on at least a portion of the first polymeric layer, wherein the thickness of the first polymeric layer is greater than the thickness of the second polymeric layer and the second polymeric layer comprises a self-doped polymer; and a capture molecule in physical communication with the second polymeric layer; wherein the substrate is sufficiently insulating to prevent a first microelectrode of the array from being in electrical communication with a second microelectrode of the array and a passivation layer disposed on at least a portion in between the substrate and a connection point for each microelectrode.

2. The electrochemical biosensor array of claim 1, wherein each microelectrode further comprises a multivalent metal cation interposed between the capture molecule and the second polymeric layer.

3. The electrochemical biosensor array of claim 1, wherein the first and/or second polymeric layer is electropolymerized on the conducting electrode material.

4. The electrochemical biosensor array of claim 1, wherein the first polymeric layer exchanges ions with an introduced solution when the first polymeric layer is polarized.

5. The electrochemical biosensor array of claim 1, wherein the first polymeric layer is adapted to absorb anions or expel cations when a positive potential is applied to the conducting electrode material and/or wherein the first polymeric layer is adapted to expel anions or absorb cations when a negative potential is applied to the conducting electrode material.

6. The electrochemical biosensor array of claim 1, wherein the second polymeric layer provides attachment points for the capture biomolecule.

7. The electrochemical biosensor array of claim 1, wherein the capture molecule is a protein selected to interact with another protein, a ligand, a lipid, a carbohydrate, a drug, or a polynucleotide; a polynucleotide selected to interact with another polynucleotide, a protein, a ligand, or a drug; an antibody selected to interact with an antigen; a carbohydrate selected to interact with a protein; a lipid selected to interact with a protein; a drug selected to interact with a protein or a polynucleotide; or an antigen selected to interact with an antibody.

8. The electrochemical biosensor array of claim 1, further comprising a barrier wall to isolate a first microelectrode from a second microelectrode and/or a barrier wall to isolate a first group of microelectrodes from a second group of microelectrodes.

9. The electrochemical biosensor array of claim 1, wherein the passivation layer is sufficiently insulating to prevent electrical communication between deposited components of nearby microelectrodes.

10. A biosensor instrument, comprising: a biosensor array comprising an array of microelectrodes disposed on a substrate, wherein each microelectrode comprises: a conducting electrode material disposed on a portion of the substrate; a connection point material disposed on a different portion of the substrate; a first polymeric layer disposed on at least a portion of the conducting electrode material; a second polymeric layer disposed on at least a portion of the first polymeric layer, wherein the thickness of the first polymeric layer is greater than the thickness of the second polymeric layer and the second polymeric layer comprises a self-doped polymer; a passivation layer disposed on at least a portion in between the substrate and the connection point for each microelectrode; and a capture molecule in physical communication with the second polymeric layer; a printed circuit board comprising: signal processing circuitry; and a plurality of connection points corresponding in number to the connection points of the biosensor array; wherein the substrate is sufficiently insulating to prevent a first microelectrode of the array from being in electrical communication with a second microelectrode of the array; wherein the connection points of the biosensor array are bound to the connection points of the printed circuit board; and wherein a reaction vessel is defined by the bond between the biosensor array and the printed circuit board.

11. The biosensor instrument of claim 10, further comprising at least one of the following: a reference electrode and a counter/auxiliary electrode; one reference electrode and one counter/auxiliary electrode for each microelectrode in the biosensor array; an electrochemical workstation; a signal processing mechanism, wherein the signal processing mechanism comprises data transfer and evaluation software protocols configured to transform raw data into diagnostic information; a temperature control mechanism; or a fluid control mechanism.

* * * * *